(12) United States Patent
Wong et al.

(10) Patent No.: US 10,421,968 B2
(45) Date of Patent: Sep. 24, 2019

(54) AMPHIPHILIC DENDRIMERS COMPLEXED WITH SIRNA FOR TREATMENT OF CANCER

(71) Applicants: Versitech Limited, Hong Kong (CN); Centre National de la Recherche Scientifique, Paris (FR); Université d'Aix-Marseille, Marseilles (FR); The Chinese University of Hong Kong, Hong Kong (CN)

(72) Inventors: Alice S. T. Wong, Hong Kong (CN); Jing Ma, Hong Kong (CN); Ling Peng, Paris (FR); K. W. Lo, Hong Kong (CN)

(73) Assignees: Versitech Limited, Hong Kong (CN); Centre National de la Recherche Scientifique, Paris (FR); Université d'Aix-Marseille, Paris (FR); The Chinese University of Hong Kong, Hong Kong (CN)

( * ) Notice: Subject to any disclaimer, the term of this patent is extended or adjusted under 35 U.S.C. 154(b) by 66 days.

(21) Appl. No.: 15/459,806

(22) Filed: Mar. 15, 2017

(65) Prior Publication Data

US 2018/0265872 A1 Sep. 20, 2018

(51) Int. Cl.
| | | |
|---|---|---|
| *C12N 15/113* | (2010.01) | |
| *A61K 47/56* | (2017.01) | |
| *A61P 35/00* | (2006.01) | |

(52) U.S. Cl.
CPC .......... *C12N 15/1135* (2013.01); *A61K 47/56* (2017.08); *A61P 35/00* (2018.01); *C12N 2310/14* (2013.01); *C12N 2320/32* (2013.01)

(58) Field of Classification Search
None
See application file for complete search history.

(56) References Cited

U.S. PATENT DOCUMENTS 3,773,919 A 11/1973 Boswell et al.

FOREIGN PATENT DOCUMENTS

EP 0058481 A1 8/1982

OTHER PUBLICATIONS

Wakefield, et al. (2012) "Bcl3 Selectively Promotes Metastasis of ERBB2-Driven Mammary Tumors". Cancer Res., v.73:745-55. (Year: 2012).*

Biswas, Swati et al., Dendrimers for siRNA Delivery, Pharmaceuticals, Feb. 4, 2013, 6(2):161-183, Basel, Switzerland.
Chung, Grace Tin-Yun et al., Constitutive activation of distinct NF-κB signals in EBV-associated nasopharyngeal carcinoma, Journal of Pathology, Sep. 3, 2013, 231(3):311-322, John Wiley & Sons, Ltd.
Lam, Jenny K.W. et al., What is the Future of SiRNA Therapeutics? Journal of Drug Design and Research, Nov. 14, 2014, 1(1):1005, pp. 1-2.
Liu, Xiaoxuan et al., Promoting siRNA delivery via enhanced cellular uptake using an arginine-decorated amphiphilic dendrimer, Nanoscale, 2015, 7(9):3867-3875, The Royal Society of Chemistry.
Sidman, Kenneth R. et al., Controlled Release of Macromolecules and Pharmaceuticals from Synthetic Polypeptides Based on Glutamic Acid, Biopolymers, Jan. 1983, 22(1):547-556, John Wiley & Sons, Inc.
Zhang, Yuan et al., Systemic delivery of gemcitabine triphosphate via LCP nanoparticles for NSCLC and pancreatic cancer therapy, Biomaterials, 2013, 34(13):3447-3458, Elsevier Ltd.
Chung, G. T. et al., "Constitutive activation of distinct NF-κB signals in EBV-associated nasopharyngeal carcinoma," *Journal of Pathology*, 2013, 231:311-322, Pathological Society of Great Britain and Ireland, along with Table S3 Sequences of primers and siRNA used in this study.
Wei, T. et al., "Anticancer drug nanomicelles formed by self-assembling amphiphilic dendrimer to combat cancer drug resistance," *PNAS*, Mar. 10, 2015, 112(10):2978-2983.
Liu, X. et al., "Adaptive amphiphilic dendrimer based nanoassemblies as robust and versatile siRNA delivery systems," *Angew Chem Int Ed Engl.*, Oct. 27, 2014, 53(44):11822-11827.
Yu, T. et al., "An Amphiphilic Dendrimer for Effective Delivery of Small Interfering RNA and Gene Silencing In Vitro and In Vivo," *Angew Chem Int Ed*, 2012, 51:8478-8484, Wiley-VCH Verlag GmbH & Co. KGaA, Weinheim.
Liu, C. et al., "Arginine-Terminated Generation 4 PAMAM Dendrimer as an Effective Nanovector for Functional siRNA Delivery in Vitro and in Vivo," *Bioconjugate Chemistry*, 2014, 25:521-532, American Chemical Society.

* cited by examiner

*Primary Examiner* — Jennifer Pitrak McDonald
(74) *Attorney, Agent, or Firm* — Saliwanchik, Lloyd & Eisenschenk

(57) ABSTRACT

The invention pertains to amphiphilic dendrimers complexed with Bcl3 siRNA. The amphiphilic dendriplexes described herein are biodegradable and exhibit enhanced siRNA delivery. The amphiphilic dendriplexes containing Bcl3 siRNA inhibit cancer cell/tumor growth in vitro and in vivo without toxicity. Accordingly, an embodiment of the invention provides a method of treating a cancer, particularly, nasopharyngeal carcinoma, by administering to a subject in need thereof, a therapeutic amount of amphiphilic dendrimers complexed with Bcl3 siRNA. Pharmaceutical compositions containing the amphiphilic dendrimers complexed with Bcl3 siRNA are also provided.

9 Claims, 3 Drawing Sheets
Specification includes a Sequence Listing.

SEQUENCE LISTING

<160> NUMBER OF SEQ ID NOS: 5

<210> SEQ ID NO 1
<211> LENGTH: 25
<212> TYPE: RNA
<213> ORGANISM: Artificial Sequence
<220> FEATURE:
<223> OTHER INFORMATION: Bcl3 siRNA

<400> SEQUENCE: 1
agcugcacca ugcuaaggcu guugu                                    25

<210> SEQ ID NO 2
<211> LENGTH: 20
<212> TYPE: DNA
<213> ORGANISM: Artificial Sequence
<220> FEATURE:
<223> OTHER INFORMATION: Sense primer for amplification of Bcl3

<400> SEQUENCE: 2
ctcaagaact gccacaacga                                          20

<210> SEQ ID NO 3
<211> LENGTH: 20
<212> TYPE: DNA
<213> ORGANISM: Artificial Sequence
<220> FEATURE:
<223> OTHER INFORMATION: Anti-sense primer for amplification of Bcl3

<400> SEQUENCE: 3
agggtgagga ggatggtgat                                          20

<210> SEQ ID NO 4
<211> LENGTH: 24
<212> TYPE: DNA
<213> ORGANISM: Artificial Sequence
<220> FEATURE:
<223> OTHER INFORMATION: Sense primer for amplification of  Beta-actin

<400> SEQUENCE: 4
tcaccgaggc ccctctgaac ccta                                     24

<210> SEQ ID NO 5
<211> LENGTH: 24
<212> TYPE: DNA
<213> ORGANISM: Artificial Sequence
<220> FEATURE:
<223> OTHER INFORMATION: Anti-sense primer for amplification of  Beta-
      actin

<400> SEQUENCE: 5
ggcagtaatc tccttctgca tcct                                     24

AMPHIPHILIC DENDRIMERS COMPLEXED WITH SIRNA FOR TREATMENT OF CANCER

The Sequence Listing for this application is labeled "Sequence-Listing_ST25.txt", which was created on Mar. 14, 2017, and is 2 KB. The entire content is incorporated herein by reference in its entirety.

BACKGROUND OF THE INVENTION

Nasopharyngeal carcinoma (NPC) is a type of head and neck cancer. Radiotherapy is an effective treatment for NPC patients with early disease; however, therapeutic strategies remain less successful for patients presenting with metastatic disease or refractory cancer relapse. Bcl3 is an established oncogene in hematologic malignancies. Bcl3 can repress the activation of NF-κB signaling cascade by direct binding to p50, p52, RelA, RelB, or cRel. p50/p50/Bcl3 is the major NF-κB complex being constitutively activated in NPC. Constitutive activation of distinct NF-κB complexes via p50/p50/Bcl3 was found in almost all EBV-positive NPC cells C666-1 and primary NPCs, but not in normal cells. Bcl3 inhibitor has been developed as anti-breast cancer reagent, is shown to reduce 80% metastasis, and is in Phase I clinical trial. Small interfering RNA (siRNA) technology has been applied in gene silencing for cancer treatment in recent years. Over 40 siRNA-based therapeutics have reached the clinical trial stage for treatment of a variety of diseases including cancers, infections, cardiovascular diseases, and genetic disorders. Since naked siRNA is highly unstable, siRNA therapy requires vectors for siRNA delivery. Current dendrimers used as siRNA carriers have limited efficacy, certain toxicity and are not biodegradable.

BRIEF SUMMARY OF THE INVENTION

The invention describes that amphiphilic dendrimers form stable dendriplexes with Bcl3 siRNA. The amphiphilic dendrimers (AmDM) used in this invention exhibit enhanced properties in siRNA delivery. The AmDM significantly improve gene silencing efficiency, enhance siRNA cellular uptake, and exhibit no discernible cytotoxicity compared to other dendrimers. The AmDM containing Bcl3 siRNA inhibit cancer cell/tumor growth in vitro and in vivo without toxicity. Accordingly, an embodiment of the invention provides a method of treating a cancer, particularly, NPC, by administering to a subject in need thereof, a therapeutic amount of amphiphilic dendrimers complexed with Bcl3 siRNA. Pharmaceutical compositions containing amphiphilic dendrimers complexed with Bcl3 siRNA are also provided.

BRIEF DESCRIPTION OF THE SEQUENCES

Figure 1:
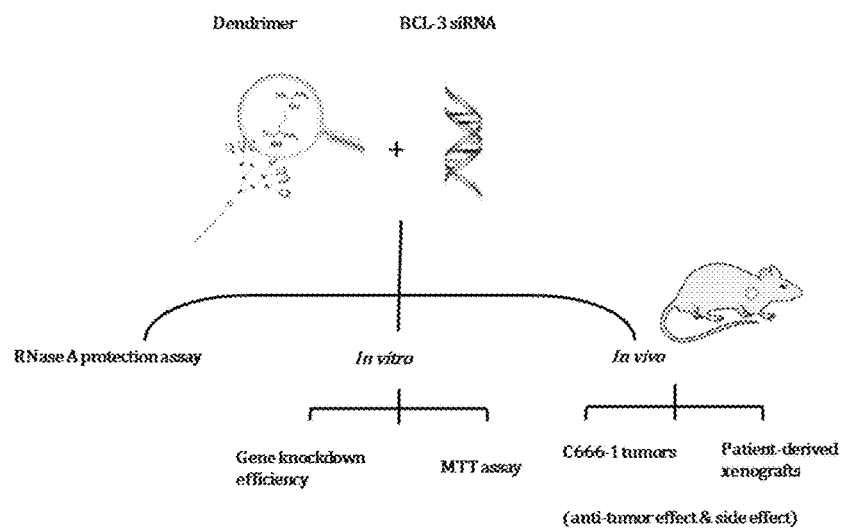
FIG. 1 shows scheme graph of AmDM complexed with Bcl3 siRNA in treating NPC.

SEQ ID NO: 1: An example of a sequence of Bcl3 siRNA
SEQ ID NO: 2: Sense primer for amplification of Bcl3.
SEQ ID NO: 3: Anti-sense primer for amplification of Bcl3.
SEQ ID NO: 4: Sense primer for amplification of β-actin.
SEQ ID NO: 5: Anti-sense primer for amplification of β-actin.

DETAILED DISCLOSURE OF THE INVENTION

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising". The transitional terms/phrases (and any grammatical variations thereof) "comprising," "comprises," "comprise," include the phrases "consisting essentially of," "consists essentially of," "consisting," and "consists." The phrases "consisting essentially of" or "consists essentially of" indicate that the claim encompasses embodiments containing the specified materials or steps and those that do not materially affect the basic and novel characteristic(s) of the claim.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed. In the context of compositions containing amounts of ingredients where the terms "about" or "approximately" are used, these compositions contain the stated amount of the ingredient with a variation (error range) of 0-10% around the value (X±10%).

When ranges are used herein, such as for dose ranges, combinations and subcombinations of ranges (e.g., subranges within the disclosed range), specific embodiments therein are intended to be explicitly included.

"Treatment", "treating", "palliating" and "ameliorating" (and grammatical variants of these terms), as used herein, are used interchangeably. These terms refer to an approach for obtaining beneficial or desired results including but not limited to therapeutic benefit. A therapeutic benefit is achieved with the eradication or amelioration of one or more of the physiological symptoms associated with the underlying disorder such that an improvement is observed in the patient, notwithstanding that the patient may still be afflicted with the underlying disorder.

As used herein, the term "cancer" refers to the presence of cells possessing abnormal growth characteristics, such as uncontrolled proliferation, immortality, metastatic potential, rapid growth and proliferation rate, perturbed oncogenic signaling, and certain characteristic morphological features. This includes but is not limited to the growth of: (1) benign or malignant cells (e.g., tumor cells) that correlates with overexpression of a serine/threonine kinase; or (2) benign or malignant cells (e.g., tumor cells) that correlates with abnormally high levels of serine/threonine kinase activity or lipid kinase activity. Non-limiting serine/threonine kinases implicated in cancer include but are not limited to PI-3K mTOR, and AKT. Exemplary lipid kinases include but are not limited to PI3 kinases such as PBKα, PBKβ, PBKδ, and PBKγ.

The phrase "pharmaceutically effective amount" refers to that amount of a therapeutic agent described herein that is sufficient to effect the intended application including but not limited to disease treatment. The pharmaceutically effective amount may vary depending upon the intended application or the subject and cancer condition being treated, e.g., the weight and age of the subject, the severity of the cancer, and the manner of administration. The term also applies to a dose that will induce a particular response in target cells, e.g., reduction of proliferation or downregulation of activity of a target protein. The specific dose will vary depending on the particular therapeutic agent, the dosing regimen to be followed, whether it is administered in combination with other compounds, timing of administration, the tissue to which it is administered, and the physical delivery system in which it is carried.

A "sub-therapeutic amount" of an agent is an amount less than the effective amount for that agent, but which when combined with an effective or sub-therapeutic amount of another agent or therapy can produce a desired result, due to, for example, synergy in the resulting efficacious effects (e.g., therapeutic benefit) for the patient, or reduced side effects associated with the compounds administered to the patient. Typical therapeutic amounts for an agent, as disclosed herein, can be ascertained from various publicly available sources (e.g., drugs.com, The Physician's Desk Reference, or scientific literature).

As used herein, "a therapeutic agent" or "agents" refers to siRNA against Bcl3 mRNA. A therapeutic agent can be "naked," i.e., without being complexed with a delivery agent or complexed with a delivery agent, particularly, an amphiphilic dendrimer. An siRNA against Bcl3 protein that is complexed with an amphiphilic dendrimer is called "Bcl3 siRNA amphiphilic dendriplex" or "Bcl3 siRNA dendriplex." Similarly, an NS siRNA that is complexed with an amphiphilic dendrimer is called "NS siRNA amphiphilic dendriplex" or "NS siRNA dendriplex." An example of an siRNA against Bcl3 mRNA is provided by SEQ ID NO: 1. A person of ordinary skill in the art can design additional siRNAs against Bcl3 mRNA and such embodiments are within the purview of the invention.

A "therapeutic effect," as used herein, encompasses a therapeutic benefit as described above. This includes delaying the onset of symptoms of cancer, slowing, halting, or reversing the progression of cancer.

"Subject" refers to an animal, such as a mammal, for example a human. The methods described herein can be useful in both pre-clinical human therapeutics and veterinary applications. In some embodiments, the subject is a mammal (such as an animal model of disease), and in some embodiments, the subject is human. The terms "subject" and "patient" can be used interchangeably.

In certain embodiments, the cancer that can be treated according to the methods described herein include, but are not limited to: Acanthoma, Acinic cell carcinoma, Acoustic neuroma, Acral lentiginous melanoma, Acrospiroma, Acute eosinophilic leukemia, Acute lymphoblastic leukemia, Acute megakaryoblastic leukemia, Acute monocytic leukemia, Acute myeloblastic leukemia with maturation, Acute myeloid dendritic cell leukemia, Acute myeloid leukemia, Acute promyelocytic leukemia, Adamantinoma, Adenocarcinoma, Adenoid cystic carcinoma, Adenoma, Adenomatoid odontogenic tumor, Adrenocortical carcinoma, Adult T-cell leukemia, Aggressive NK-cell leukemia, AIDS-related cancers, AIDS-related lymphoma, Alveolar soft part sarcoma, Ameloblastic fibroma, Anal cancer, Anaplastic large cell lymphoma, Anaplastic thyroid cancer, Angioimmunoblastic T-cell lymphoma, Angiomyolipoma, Angiosarcoma, Appendix cancer, Astrocytoma, Atypical teratoid rhabdoid tumor, Basal cell carcinoma, Basal-like carcinoma, B-cell leukemia, B-cell lymphoma, Bellini duct carcinoma, Biliary tract cancer, Bladder cancer, Blastoma, Bone cancer, Bone tumor, Brain stem lipoma, Brain tumor, Breast cancer, Brenner tumor, Bronchial tumor, Bronchioloalveolar carcinoma, Brown tumor, Burkitt's lymphoma, Cancer of unknown primary site, Carcinoid Tumor, Carcinoma, Carcinoma in situ, Carcinoma of the penis, Carcinoma of unknown primary site, Carcinosarcoma, Castleman's Disease, Central nervous system embryonal tumor, Cerebellar astrocytoma, Cerebral astrocytoma, Cervical cancer, Cholangiocarcinoma, Chondroma, Chondrosarcoma, Chordoma, Choriocarcinoma, Choroid plexus papilloma, Chronic lymphocytic leukemia, Chronic monocytic leukemia, Chronic myelogenous leukemia, Chronic myeloproliferative disorder, Chronic neutrophilic leukemia, Clear-cell tumor, Colon cancer, Colorectal cancer, Craniopharyngioma, Cutaneous T-cell lymphoma, Degos disease, Dermatofibrosarcoma protuberans, Dermoid cyst, Desmoplastic small round cell tumor, Diffuse large B cell lymphoma, Dysembryoplastic neuroepithelial tumor, Embryonal carcinoma, Endodermal sinus tumor, Endometrial cancer, Endometrial uterine cancer, Endometrioid tumor, Enteropathy-associated T-cell lymphoma, Ependymoblastoma, Ependymoma, Epithelioid sarcoma, Erythroleukemia, Esophageal cancer, Esthesioneuroblastoma, Ewing family of tumor, Ewing family sarcoma, Ewing's sarcoma, Extracranial germ cell tumor, Extragonadal germ cell tumor, Extrahepatic bile duct cancer, Extramammary Paget's disease, Fallopian tube cancer, Fetus in fetu, Fibroma, Fibrosarcoma, Follicular lymphoma, Follicular thyroid cancer, Gallbladder Cancer, Gallbladder cancer, Ganglioglioma, Ganglioneuroma, Gastric cancer, Gastric lymphoma, Gastrointestinal cancer, Gastrointestinal carcinoid tumor, Gastrointestinal stromal tumor, Gastrointestinal stromal tumor, Germ cell tumor, Germinoma, Gestational choriocarcinoma, Gestational trophoblastic tumor, Giant cell tumor of bone, Glioblastoma multiforme, Glioma, Gliomatosis cerebri, Glomus tumor, Glucagonoma, Gonadoblastoma, Granulosa cell tumor, Hairy Cell Leukemia, Hairy cell leukemia, Head and neck cancer, Heart cancer, Hemangioblastoma, Hemangiopericytoma, Hemangiosarcoma, Hematological malignancy, Hepatocellular carcinoma, Hepatosplenic T-cell lymphoma, Hereditary breast-ovarian cancer syndrome, Hodgkin's lymphoma, Hypopharyngeal cancer, Hypothalamic glioma, Inflammatory breast cancer, Intraocular melanoma, Islet cell carcinoma, Islet cell tumor, Juvenile myelomonocytic leukemia, Sarcoma, Kaposi's sarcoma, Kidney cancer, Klatskin tumor, Krukenberg tumor, Laryngeal cancer, Lentigo maligna melanoma, Leukemia, Leukemia, Lip and oral cavity cancer, Liposarcoma, Lung cancer, Luteoma, Lymphangioma, Lymphangiosarcoma, Lymphoepithelioma, Lymphoid leukemia, Lymphoma, Macroglobulinemia, Malignant fibrous histiocytoma, Malignant fibrous histiocytoma of bone, Malignant glioma, Malignant mesothelioma, Malignant peripheral nerve sheath tumor, Malignant rhabdoid tumor, Malignant triton tumor, MALT lymphoma, Mantle cell lymphoma, Mast cell leukemia, Mediastinal germ cell tumor, Mediastinal tumor, Medullary thyroid cancer, Medulloblastoma, Medulloepithelioma, Melanoma, Melanoma, Meningioma, Merkel Cell Carcinoma, Mesothelioma, Metastatic squamous neck cancer with occult primary, Metastatic urothelial carcinoma, Mixed mullerian tumor, Monocytic leukemia, Mouth cancer, Mucinous tumor, Multiple endocrine neoplasia syndrome, Multiple myeloma, Mycosis fungoides, Myelodysplasia disease, Myelodysplasia syndromes, Myeloid leukemia, Myeloid sarcoma, Myeloproliferative disease, Myxoma, nasal cavity cancer, Nasopharyngeal cancer, Nasopharyngeal carcinoma, Neoplasm, Neurinoma, Neuroblastoma, Neuroblastoma, Neurofibroma, Neuroma, Nodular melanoma, Non-Hodgkin's lymphoma, Nonmelanoma skin cancer, Non-small cell lung cancer, Ocular oncology, Oligoastrocytoma, Oligodendroglioma, Oncocytoma, Optic nerve sheath meningioma, Oral cancer, Oropharyngeal cancer, Osteosarcoma, Osteosarcoma, Ovarian cancer, Ovarian epithelial cancer, Ovarian germ cell tumor, Ovarian low malignant potential tumor, Paget's disease of the breast, Pancoast tumor, Pancreatic cancer, Papillary thyroid cancer, Papillomatosis, Paraganglioma, Paranasal sinus cancer, Parathyroid cancer, Penile cancer, Perivascular epithelioid cell tumor, Pharyngeal cancer, Pheochromocytoma, Pineal parenchymal tumor of intermediate differentiation, Pineoblastoma, Pituicytoma, Pituitary adenoma, Pituitary tumor, Plasma cell neoplasm, Pleuropulmonary blastoma, Polyembryoma, precursor T-lymphoblastic lymphoma, Primary central nervous system lymphoma, Primary effusion lymphoma, Primary hepatocellular cancer, Primary liver cancer, Primary peritoneal cancer, Primitive neuroectodermal tumor, Prostate cancer, Pseudomyxoma peritonei, Rectal cancer, Renal cell carcinoma, Respiratory tract carcinoma involving the NUT gene on chromosome 15, Retinoblastoma, Rhabdomyoma, Rhabdomyosarcoma, Richter's transformation, Sacrococcygeal teratoma, Salivary gland cancer, Sarcoma, Schwannomatosis, Sebaceous gland carcinoma, Secondary neoplasm, Seminoma, Serous tumor, Sertoli-Leydig cell tumor, Sex cord-stromal tumor, Sezary Syndrome, Signet ring cell carcinoma, Skin cancer, Small blue round cell tumor, Small cell carcinoma, Small cell lung cancer, Small cell lymphoma, Small intestine cancer, Soft tissue sarcoma, Somatostatinoma, Soot wart, Spinal cord tumor, Spinal tumor, Splenic marginal zone lymphoma, Squamous cell carcinoma, Stomach cancer, Superficial spreading melanoma, Supratentorial primitive neuroectodermal tumor, Surface epithelial-stromal tumor, Synovial sarcoma, T-cell acute lymphoblastic leukemia, T-cell large granular lymphocyte leukemia, T-cell leukemia, T-cell lymphoma, T-cell prolymphocytic leukemia, Teratoma, Terminal lymphatic cancer, Testicular cancer, Thecoma, Throat cancer, Thymic carcinoma, Thymoma, Thyroid cancer, Transitional Cell Cancer of renal pelvis and ureter, Transitional cell carcinoma, Urachal cancer, Urethral cancer, Urogenital neoplasm, Uterine sarcoma, Uveal melanoma, Vaginal cancer, Verner-Morrison syndrome, Verrucous carcinoma, Visual pathway glioma, Vulvar cancer, Waldenstrom's macroglobulinemia, Warthin's tumor, Wilms' tumor, or any combinations thereof.

In one embodiments, the cancer that can be treated according to the methods described herein is NPC. NPC refers to the most common cancer originating in the nasopharynx.

siRNA is a class of double-stranded RNA molecules that are about 20-25 base pairs in length and that operate within the RNA interference (RNAi) pathway and degrade a target mRNA to prevent expression of the protein encoded by the target mRNA.

The term "dendrimer" refers to repetitively branched molecules. Dendrimers have an organized structure and are characterized by structural perfection. Dendrimers are monodisperse and highly symmetric compounds. Dendrimers are tree-like molecules with various cavities in the interior.

The term "amphiphilic" describes a chemical compound possessing both hydrophilic (water-loving, polar) and lipophilic (fat-loving) properties. The phrase "amphiphilic dendrimer" refers to repetitively branched molecules having amphiphilic properties.

The term "amphiphilic dendriplex" describes "an amphiphilic dendrimer complexed with an siRNA." The phrase "an amphiphilic dendrimer complexed with an siRNA" describes a dendrimer binding siRNA to form a complex.

"Bcl3" refers to "B-Cell CLL/Lymphoma 3" gene/protein/mRNA. Synonyms of Bcl3 are known in the art and can be found, for example, on world-wide website: genecards.org/cgi-bin/carddisp.pl?gene=Bcl3

The phrase "patient derived xenograft" refers to a xenograft created when a cancerous tissue from a patient's primary tumor is implanted into an immunodeficient mouse.

The enzyme "RNase A" refers to an enzyme that can digest/degrade RNA.

AmDMs are used as siRNA carriers or nano-carriers to delivery Bcl3 siRNA or NS siRNA in nasopharyngeal carcinoma. Bcl3 siRNA and amphiphilic dendrimer were formed in medium and transfected into C666-1 cells at an N/P ratio of 5 and siRNA concentration of 10 nM. The siRNA dendriplexes protected the siRNA from RNase A digestion for at least 30 min. The Bcl3 gene expression knock down efficacy reached over 80%. The siRNA dendriplexes showed significant anti-proliferation effect in C666-1 cells. The anti-tumor activity was also investigated in C666-1 xenografts and patients' xenografts (xeno-2117 and xeno-C15). The tumor size significant decreased since the second time of i.v. injection while there was no obvious difference in body weight change in all three xenografts.

Accordingly, an embodiment of the invention provides a method for treating a cancer, particularly, NPC, the method comprising administering to a patient in need thereof a composition comprising a pharmaceutically effective amount of an amphiphilic dendrimer complexed with a Bcl3 siRNA.

In one embodiment, the amphiphilic dendriplexes administered to a subject has an N/P ratio of between 2.5 to 15, preferably, between 5 to 15, more particularly, between 5 to 10, and even more preferably, about 5.

N/P ratio is the ratio of available surface amines of the dendrimer to the number of phosphates in siRNA molecule.

In one embodiment, the Bcl3 siRNA amphiphilic dendriplexes are administered to a subject in an amount that produces Bcl3 siRNA concentration in the subject's body, particularly, in the target tumor/cancer cells, of 2.5 nM to 50 nM, preferably, 10 nM to 50 nM, more preferably, 20 nM to 50 nM, and even more preferably, about 10 nM or about 20 nM.

In a particularly embodiment, the Bcl3 siRNA has the sequence of SEQ ID NO: 1.

In certain embodiments of the invention, an anti-cancer therapy described herein is administered in addition to one or more additional anticancer therapies. In further embodiments of the invention, an anti-cancer therapy described herein is administered in addition to one or more additional anticancer therapies, wherein at least one of the therapies is administered in a sub-therapeutic amount. In an even further embodiment, an anti-cancer therapy described herein is administered in a sub-therapeutic amount in addition to one or more additional anticancer therapies, wherein each of the one or more additional therapies are administered in a sub-therapeutic amount.

Such additional therapies include, but are not limited to, radiotherapy, chemotherapy, surgery, immunotherapy, small molecule, kinase inhibition and/or monoclonal antibody therapy (e.g., rituximab for the treatment of B-cell lymphomas). In an embodiment of the invention the additional therapy comprises administration of temozolomide (TMZ).

In one embodiment, an anti-cancer therapy described herein is administered in addition to one or more of: Abiraterone Acetate, Abitrexate (Methotrexate), Abraxane (Paclitaxel Albumin-stabilized Nanoparticle Formulation), ABVD, ABVE, ABVE-PC, AC, AC-T, Adcetris (Brentuximab Vedotin), ADE, Adriamycin (Doxorubicin Hydrochloride), Adrucil (Fluorouracil), Afinitor (Everolimus), Aldara (Imiquimod), Aldesleukin, Alemtuzumab, Alimta (Pemetrexed Disodium), Aloxi (Palonosetron Hydrochloride), Ambochlorin (Chlorambucil), Amboclorin (Chlorambucil), Aminolevulinic Acid, Anastrozole, Aprepitant, Arimidex (Anastrozole), Aromasin (Exemestane), Arranon (Nelarabine), Arsenic Trioxide, Arzerra (Ofatumumab), Asparaginase *Erwinia chrysanthemi*, Avastin (Bevacizumab), Axitinib, Azacitidine, BEACOPP, Bendamustine Hydrochloride, BEP, Bevacizumab, Bexarotene, Bexxar (Tositumomab and I 131 Iodine Tositumomab), Bleomycin, Bortezomib, Bosulif (Bosutinib), Bosutinib, Brentuximab Vedotin, Cabazitaxel, Cabozantinib-S-Malate, CAF, Campath (Alemtuzumab), Camptosar (Irinotecan, ydrochloride), Capecitabine, CAPOX, Carboplatin, CARBOPLATIN-TAXOL, Carfilzomib, CeeNU (Lomustine), Cerubidine (Daunorubicin Hydrochloride), Cervarix (Recombinant HPV Bivalent Vaccine), Cetuximab, Chlorambucil, CHLORAMBUCIL-PREDNISONE, CHOP, Cisplatin, Clafen (Cyclophosphamide), Clofarabine, Clofarex (Clofarabine), Clolar (Clofarabine), CMF, Cometriq (Cabozantinib-S-Malate), COPP, Cosmegen (Dactinomycin), Crizotinib, CVP (COP), Cyclophosphamide, Cyfos (Ifosfamide), Cytarabine, Cytarabine, Liposomal, Cytosar-U (Cytarabine), Cytoxan (Cyclophosphamide), Dacarbazine, Dacogen, (Decitabine), Dactinomycin, Dasatinib, Daunorubicin Hydrochloride, Decitabine, Degarelix, Denileukin, iftitox, Denosumab, DepoCyt (Liposomal Cytarabine), DepoFoam (Liposomal Cytarabine), Dexrazoxane hydrochloride, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Efudex (Fluorouracil), Elitek (Rasburicase), Ellence (Epirubicin Hydrochloride), Eloxatin (Oxaliplatin), Eltrombopag Olamine, Emend (Aprepitant), Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase *Erwinia chrysanthemi*), Etopophos (Etoposide Phosphate), Etoposide, Etoposide Phosphate, Evacet (Doxorubicin Hydrochloride Liposome), Everolimus, Evista (Raloxifene Hydrochloride), Exemestane, Fareston (Toremifene), Faslodex (Fulvestrant), FEC, Femara (Letrozole), Filgrastim, Fludara (Fludarabine Phosphate), Fludarabine Phosphate, Fluoroplex (Fluorouracil), Fluorouracil, Folex (Methotrexate), Folex PFS (Methotrexate), FOLFIRI, FOLFIRI-BEVACIZUMAB, FOLFIRINOX, FOLFOX, Folotyn (Pralatrexate), FU-LV, Fulvestrant, Gardasil (Recombinant HPV Quadrivalent Vaccine), Gefitinib, Gemcitabine Hydrochloride, GEMCITABINE-CISPLATIN, Gemtuzumab Ozogamicin, Gemzar (Gemcitabine, ydrochloride), Gleevec (Imatinib Mesylate), Glucarpidase, Halaven (Eribulin Mesylate), Herceptin (Trastuzumab), HPV Bivalent Vaccine, Recombinant, HPV Quadrivalent Vaccine (Recombinant), Hycamtin (Topotecan Hydrochloride), Ibritumomab Tiuxetan, ICE, Iclusig (Ponatinib Hydrochloride), Ifex (Ifosfamide), Ifosfamide, Ifosfamidum (Ifosfamide), Imatinib Mesylate, Imiquimod, Inlyta (Axitinib), Ipilimumab, Iressa (Gefitinib), Irinotecan Hydrochloride, Istodax (Romidepsin), Ixabepilone, Ixempra (Ixabepilone), Jakafi (Ruxolitinib Phosphate), Jevtana (Cabazitaxel), Keoxifene (Raloxifene Hydrochloride), Kepivance (Palifermin), Kyprolis (Carfilzomib), Lapatinib Ditosylate, Lenalidomide, Letrozole, Leucovorin Calcium, Leukeran (Chlorambucil), Leuprolide Acetate, Levulan (Aminolevulinic (Acid), Linfolizin (Chlorambucil), LipoDox (Doxorubicin Hydrochloride Liposome), Liposomal Cytarabine, Lomustine, Lupron (Leuprolide Acetate), Lupron Depot (Leuprolide Acetate), Lupron Depot-Ped (Leuprolide Acetate), Lupron Depot-3 Month (Leuprolide Acetate), Lupron Depot-4 Month (Leuprolide Acetate), Marqibo (Vincristine Sulfate Liposome), Matulane (Procarbazine Hydrochloride), Mechlorethamine Hydrochloride, Mesna, Mesnex (Mesna), Methazolastone (Temozolomide), Methotrexate, Methotrexate LPF (Methotrexate), Mexate (Methotrexate), Mexate-AQ (Methotrexate), Mitomycin C, Mitozytrex (Mitomycin C), MOPP, Mozobil (Plerixafor), Mustargen (Mechlorethamine hydrochloride), Mutamycin (Mitomycin C), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Nelarabine, Neosar (Cyclophosphamide), Neupogen (Filgrastim), Nexavar (Sorafenib Tosylate), Nilotinib, Nolvadex (Tamoxifen Citrate), Nplate (Romiplostim), Ofatumumab, Omacetaxine, Mepesuccinate, Oncaspar (Pegaspargase), Ontak (Denileukin Diftitox), Oxaliplatin, Paclitaxel, Paclitaxel Albumin-stabilized Nanoparticle Formulation, Palifermin, Palonosetron Hydrochloride, Panitumumab, Paraplat (Carboplatin), Paraplatin (Carboplatin), Pazopanib Hydrochloride, Pegaspargase, Pemetrexed Disodium, Perjeta (Pertuzumab), Pertuzumab, Platinol (Cisplatin), Platinol-AQ (Cisplatin), Plerixafor, Ponatinib Hydrochloride, Pralatrexate, Prednisone, Procarbazine Hydrochloride, Proleukin (Aldesleukin), Prolia (Denosumab), Promacta (Eltrombopag Olamine), Provenge (Sipuleucel-T), Raloxifene hydrochloride, Rasburicase, R-CHOP, R-CVP, Recombinant HPV Bivalent Vaccine, Recombinant HPV, Quadrivalent Vaccine, Regorafenib, Revlimid (Lenalidomide), Rheumatrex (Methotrexate), Rituxan (Rituximab), Rituximab, Romidepsin, Romiplostim, Rubidomycin (Daunorubicin Hydrochloride), Ruxolitinib Phosphate, Sclerosol Intrapleural Aerosol (Talc), Sipuleucel-T, Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Synovir (Thalidomide), Synribo (Omacetaxine Mepesuccinate), Talc, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Temodar (Temozolomide), Temozolomide, Temsirolimus, Thalidomide, Thalomid (Thalidomide), Toposar (Etoposide), Topotecan Hydrochloride, Toremifene, Torisel (Temsirolimus), Tositumomab and I 131 Iodine Tositumomab, Totect (Dexrazoxane Hydrochloride), Trastuzumab, Treanda (Bendamustine Hydrochloride), Trisenox (Arsenic Trioxide), Tykerb (Lapatinib Ditosylate), Vandetanib, VAMP, Vectibix (Panitumumab), VeIP, Velban (Vinblastine Sulfate), Velcade (Bortezomib), Velsar (Vinblastine Sulfate), Vemurafenib, VePesid (Etoposide), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, Vismodegib, Voraxaze (Glucarpidase), Vorinostat, Votrient (Pazopanib Hydrochloride), Wellcovorin (Leucovorin Calcium), Xalkori (Crizotinib), Xeloda (Capecitabine), XELOX, Xgeva (Denosumab), Xtandi (Enzalutamide), Yervoy (Ipilimumab), Zaltrap (Ziv-Aflibercept), Zelboraf (Vemurafenib), Zevalin (Ibritumomab Tiuxetan), Zinecard (Dexrazoxane Hydrochloride), Ziv-Aflibercept, Zoledronic Acid, Zolinza (Vorinostat), Zometa (Zoledronic Acid), and Zytiga (Abiraterone Acetate).

Certain embodiments of the invention also provide a pharmaceutical composition comprising a pharmaceutically effective amount of Bcl3 siRNA amphiphilic dendriplex. The Bcl3 siRNA amphiphilic dendriplex can have the N/P ratio between the AmDM and siRNA of 2.5 to 15, preferably, 5 to 15, more preferably, 5 to 10, and even more preferably, about 5.

The pharmaceutical compositions described herein can contain one or more pharmaceutically acceptable carriers. Such pharmaceutical carriers can be liquids, such as water. The pharmaceutical composition can also comprise excipients, adjuvants, flavoring agents, etc. that facilitate processing of the active compounds into preparations that can be used pharmaceutically. Proper formulation is dependent upon the route of administration chosen. In an embodiment, the pharmaceutical composition and all ingredients contained therein are sterile.

The term "carrier" refers to a diluent, adjuvant, excipient, or vehicle with which the therapeutic agent is administered. Examples of suitable pharmaceutical carriers are described in "Remington's Pharmaceutical Sciences" by E. W. Martin. Such compositions contain therapeutic agent together with a suitable amount of carrier so as to provide the form for proper administration to the patient. The formulation should suit the enteral mode of administration.

In one embodiment, the administration of the composition can be systemic. Oral, intravenous, intra-arterial, subcutaneous, intra-peritoneal, intra-muscular, intra-ventricular, intra-nasal, transmucosal, subcutaneous, topical, rectal, and other modes of administration are contemplated.

In one embodiment, for injection, the pharmaceutical agent can be formulated in aqueous solutions, preferably in physiologically compatible buffers. For transmucosal administration, penetrants appropriate to the barrier to be permeated are used in the formulation. Such penetrants are generally known in the art. For oral administration, the active ingredient can be combined with carriers suitable for inclusion into tablets, pills, dragees, capsules, liquids, gels, syrups, slurries, suspensions and the like. Formulations can also be prepared for use in inhalation therapy. For administration by inhalation, the composition can be delivered in the form of an aerosol spray presentation from pressurized packs or a nebuliser, with the use of a suitable propellant. The composition can also be administered via inhalation or other route as a powder.

In particular embodiments, the methods according to the subject invention include administering the therapeutic composition by sustained-release systems. Suitable examples of sustained-release systems include suitable polymeric materials (such as, semi-permeable polymer matrices in the form of shaped articles, for example films, or microcapsules), suitable hydrophobic materials (for example as an emulsion in an acceptable oil) or ion exchange resins, and sparingly soluble derivatives (such as, for example, a sparingly soluble salt). Sustained-release compositions can be administered orally, parenterally, intracisternally, intraperitoneally, topically (as by powders, ointments, gels, drops or transdermal patch), or as an oral or nasal spray. Sustained-release matrices include polylactides (U.S. Pat. No. 3,773,919, EP 58,481), copolymers of L-glutamic acid and gamma-ethyl-L-glutamate (Sidman et al., Biopolymers 22:547-556, 1983, poly(2-hydroxyethyl methacrylate)); (Langer et al., J. Biomed. Mater. Res. 15:167-277, 1981; Langer, Chem. Tech. 12:98-105, 1982, ethylene vinyl acetate (Langer et al., Id.) or poly-D-(−)-3-hydroxybutyric acid (EP 133,988).

In one embodiment, implantable infusion devices may be used to provide patients with a constant and long-term dosage or infusion of a therapeutic composition. Such device can be categorized as either active or passive.

The pharmaceutical composition of the present invention may be used either alone or in combination with one or more drugs known to be effective for treating a cancer. The compositions can also be formulated in combination with at least one other agent, such as stabilizing or buffer compounds, which can be administered in any sterile, biocompatible pharmaceutical carrier, including, but not limited to, saline, buffered saline, dextrose, and water.

The composition may further contain other commonly used additives such as an anti-oxidant, a buffer, a bacteriostatic, etc., and may be formulated into an injectable formulation such as aqueous solution, suspension, emulsion, etc. or a pill, a capsule, a granule, a tablet, etc., by further adding a diluent, a dispersant, a surfactant, a binder, a lubricant, etc.

MATERIALS AND METHODS siRNA Dendriplexes Preparation.

Arginine-terminated amphiphilic dendrimer (Mw=3838 g/mol, 16 amine end groups) was dissolved in deionized, autoclaved, 0.22 m filtered water and stocked at 500 µM. Bcl3 siRNA (sequence: AGC UGC ACC AUG CUA AGG CUG UUG U (SEQ ID NO: 1) and non-specific (NS) siRNA (D-001210-02-20) were obtained from Dharmacon (Lafayette, Colo.). siRNA and dendrimer were diluted in a medium (for in vitro study) or PB S (for in vivo study) and mixed for 30 min at room temperature to form siRNA dendriplexes. N/P ratio was calculated as the ratio of available surface amines of the dendrimer to the number of phosphates in siRNA molecule.

RNase A Digestion Assay siRNA dendriplexes were incubated with RNase A (0.01 mg/ml) for 30 min at 37° C. Cold 1% SDS solution was added to release siRNA from siRNA dendriplexes. The solution was then loaded onto a 2% agarose gel containing ethidium bromide and run at 100 V in standard TBE buffer. The bands were then visualized using a UV transilluminator. Naked siRNA was used as control.

Cell Culture and siRNA Transfection

C666-1 cells were cultured in Dulbecco's modified Eagle's (DMEM) medium supplemented with 10% fetal bovine serum and 1% penicillin and streptomycin (Invitrogen, Carlsbad, Calif.) at 37° C. containing 5% $CO_2$/95% air. The cells were seeded in 24 well plate and cultured for 24 h at 37° C. The cells were then treated with indicated concentration and N/P ratio of siRNA dendriplexes for 4 days.

Reverse Transcription PCR.

Total RNA was isolated using Trizol (Invitrogen) according to the manufacturer's instructions. cDNA was synthesized using a First-strand cDNA synthesis kit (Invitrogen). PCR was performed with a set of primers: Bcl3, sense 5'-CTCAAGAACTGCCACAACGA (SEQ ID NO: 2), anti-sense 5'-AGGGTGAGGAGGATGGTGAT (SEQ ID NO: 3), and β-actin, sense 5'-TCACCGAGGCCCCTCTGAAC-CCTA-3' (SEQ ID NO: 4), anti-sense 5'-GGCAG-TAATCTCCTTCTGCATCCT-3' (SEQ ID NO: 5). β-actin served as a control.

In Vivo Tumor Model

Male athymic nude mice were purchased from Charles River Laboratories (Wilmington, Mass.). Mice of about 6 weeks were injected subcutaneously with $10^7$ cells into the right flank. Tumor volumes were calculated using the formula $(\pi/6)lw^2$, where 1 is the larger measurement and w is the smaller measurement. When the tumors reached about 30 $mm^3$, 1 mg/kg siRNA dendriplexes (N/P ratio=5) were injected intravenously. The injections were performed on the first day and fourth day. NS siRNA dendriplexes were used as control. Tumor size and body weight were measured for one week and the mice were sacrificed by cervical dislocation. The tumors and organs were excised then.

Statistical Analysis

All data were presented as the mean±SD, unless stated otherwise. The data were compared by one-way ANOVA followed by a Turkey's test among more than two groups and by unpaired Student's t-test between two groups. The differences were considered to be statistically significant when the p value was less than 0.05.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

EXAMPLE 1—AMPHIPHILIC DENDRIPLEXES CONTAINING BCL3 SIRNA TO TREAT NPC

Figure 2:
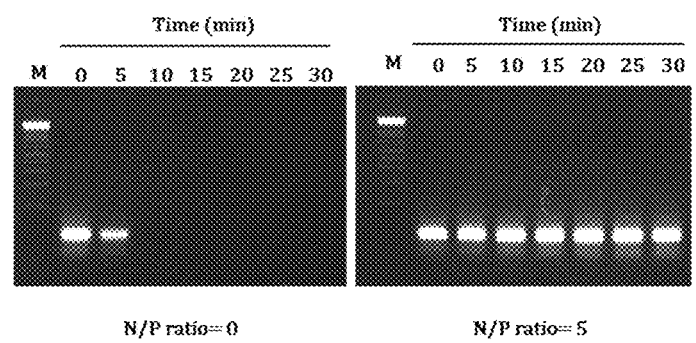
FIG. 2 shows the RNase A protection assay. AmDM complexed with Bcl3 siRNA were incubated with 0.01 mg/ml RNAse A at room temperature for 0-30 min and then incubated with 0.2% SDS at 4° C.
Figure 3:
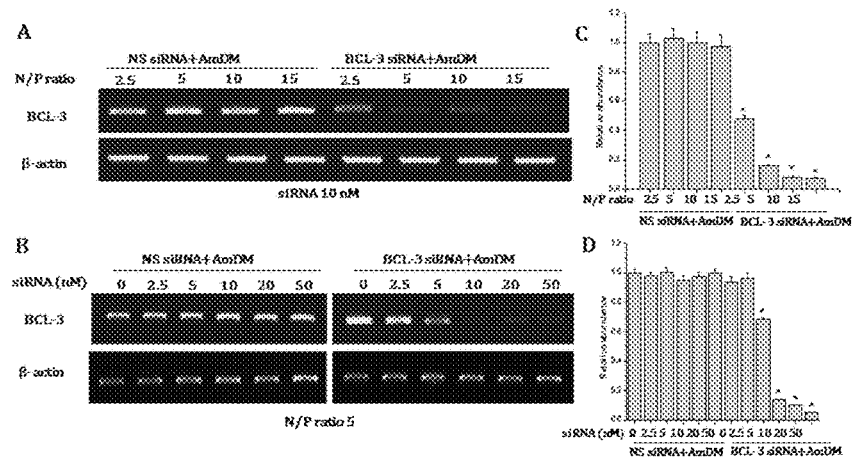
FIG. 3 shows Bcl3 gene knockdown efficacy. The knockdown efficacy was tested by PCR using AmDM complexed with Bcl3 siRNA at different N/P ratio (A and C) and different siRNA concentration (B and D). Nonspecific (NS) siRNA was used as control. Data were expressed as the mean±SEM. An asterisk indicates $p<0.05$ vs NS siRNA dendriplexes.
Figure 4:
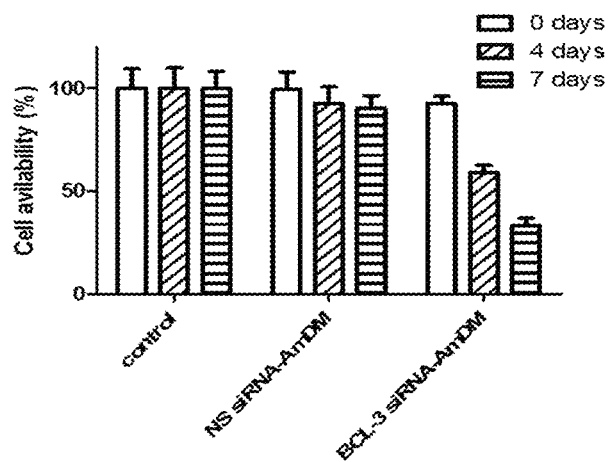
FIG. 4 shows anti-proliferation assay towards C666-1 cells. C666-1 cells were seeded in 96-wells and treated with blank, AmDM complexed with NS siRNA or Bcl3 siRNA for indicated time. MTT were then added to investigate the cell viability. Data were expressed as mean±SD (n=6), an asterisk indicates $p<0.05$ vs control.
Figure 5:
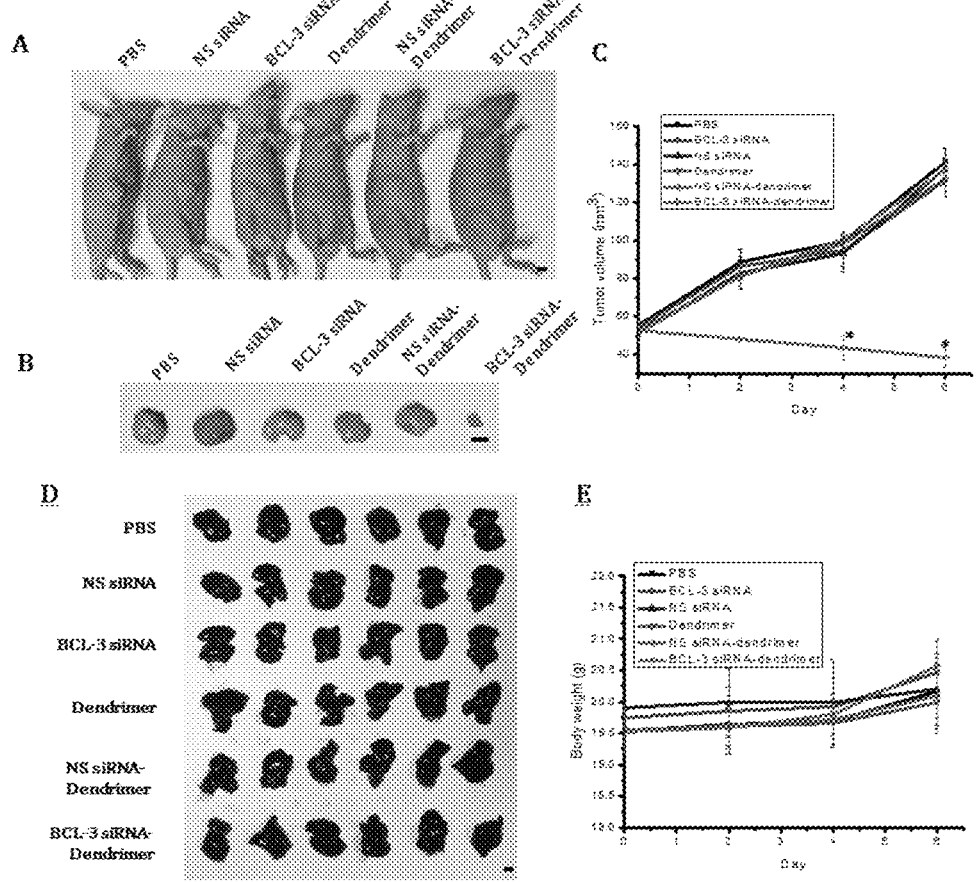
FIG. 5 shows the anti-tumor effect in C666-1 xenograft. C666-1 cells were subcutaneously injected into nude mice allowed to grow to ~50 mm$^3$. Xenografts were then treated with i.v. injection of indicated solutions. (A) and (B) Comparison of representative xenograft tumors were shown. (C) Tumors were measured by calipers every two days. (D) Comparison of liver was shown. (E) Body weights were measured by a balance. Data were expressed as mean±SEM (n=6). The bar represents 5 mm. An asterisk indicates $p<0.05$ vs NS siRNA dendriplexes.
Figure 6:
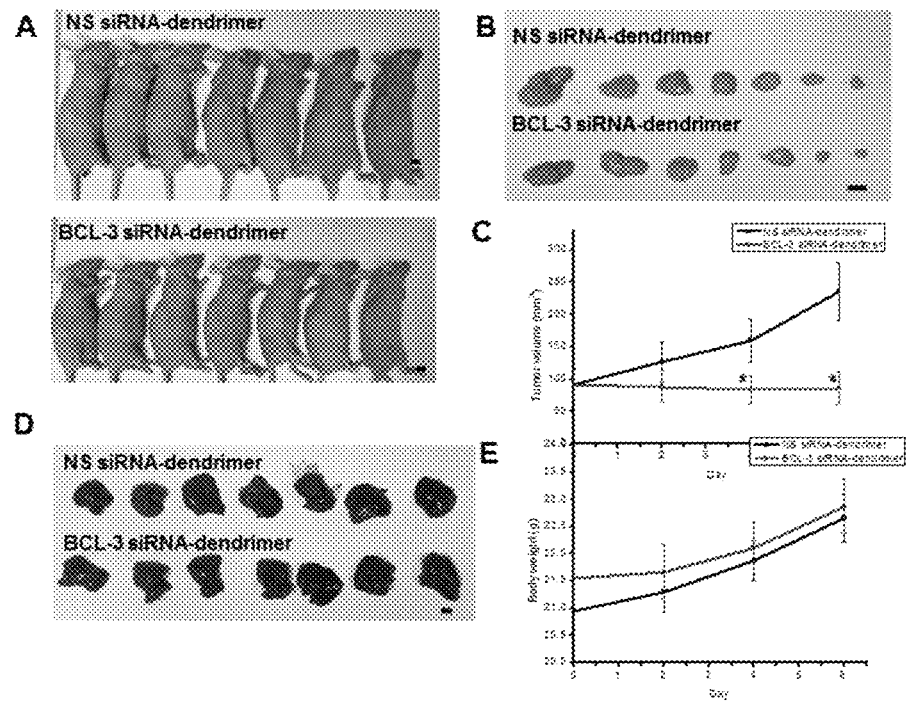
FIG. 6 shows the anti-tumor effect in patient derived xenograft (xeno-2117). Mice with xeno-2117 were then treated with i.v. injection of AmDM complexed with Bcl3 siRNA or NS siRNA. Comparison of xenograft tumors (A) and (B) were shown. (C) Tumors were measured by calipers. (D) Comparison of liver was shown. (E) Body weights were measured by a balance. The bar represents 5 mm. Data were expressed as mean±SEM (n=7). An asterisk indicates $p<0.05$ vs NS siRNA dendriplexes.
Figure 7:
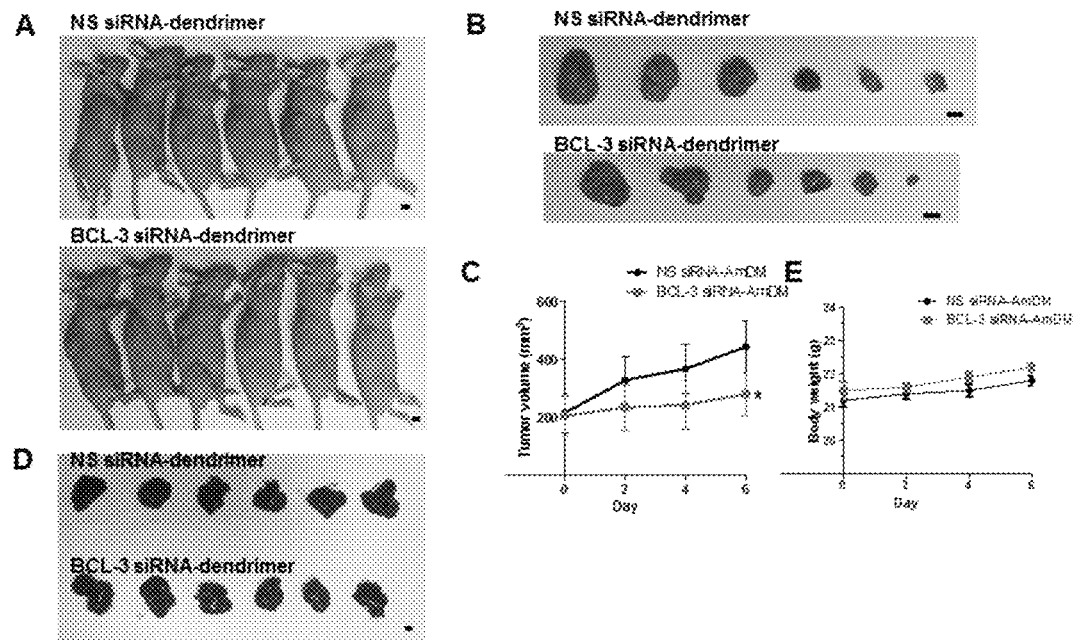
FIG. 7 shows the anti-tumor effect in patient derived xenograft (xeno-C15). Mice with xeno-C15 were then treated with i.v. injection of AmDM complexed with Bcl3 siRNA or NS siRNA. Comparison of xenograft tumors (A) and (B) were shown. (C) Tumors were measured by calipers. (D) Comparison of liver was shown. (E) Body weights were measured by a balance. The bar represents 5 mm. Data were expressed as mean±SEM (n=7). An asterisk indicates $p<0.05$ vs AmDM complexed with NS siRNA.

Amphiphilic dendrimers were used as siRNA nanocarriers to delivery Bcl3 siRNA in NPC. Bcl3 siRNA and amphiphilic dendrimer were formed in medium and transfected into C666-1 cells at an N/P ratio of 5 and siRNA concentration of 10 nM. Then the characterization of Bcl3 siRNA amphiphilic dendriplexes was evaluated by RNase A digestion assay (FIG. 2) and PCR (FIG. 3) to investigate the RNase A protection ability and gene knockdown efficiency of amphiphilic dendriplexes. MTT assay (FIG. 4) was performed to illustrate the ability of cell growth inhibition and cytotoxicity. The anti-tumor activity was evaluated in C666-1 xenografts (FIG. 5) and patients' xenografts (xeno-2117, and xeno-C15) (FIGS. 6 and 7). No significant toxicity to the liver was observed.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

1. Biswas et al., Dendrimers for siRNA Delivery, Pharmaceuticals (Basel). 2013; 6(2): 161-183.
2. Zhang et al., Systemic Delivery of Gemcitabine Triphosphate via LCP Nanoparticles for NSCLC and Pancreatic Cancer Therapy, Biomaterials. 2013; 34(13): 3447-3458.
3. Lam et al., What is the Future of SiRNA Therapeutics? J Drug Des Res. 2014; 1(1): 1005.
4. Chung et al., Constitutive activation of distinct NK-kB signals in EBV-associated nasopharyngeal carcinoma, J Pathol. 2013; 231: 311-322.
5. Liu et al., Promoting siRNA delivery via enhanced cellular uptake using an arginine-decorated amphiphilic dendrimer, Nanoscale, 2015; 7: 3867-3875.

We claim:

1. A pharmaceutical composition comprising an amphiphilic dendrimer complexed with a Bcl3 siRNA having the sequence of SEQ ID NO: 1.

2. The pharmaceutical composition of claim 1, wherein the siRNA and the amphiphilic dendrimer have an N/P ratio of 2.5 to 15, 5 to 15, or 5 to 10.

3. The pharmaceutical composition of claim 2, wherein the siRNA and the amphiphilic dendrimer have the N/P ratio of about 5.

4. A method for treating a cancer, the method comprising administering to a patient in need thereof a pharmaceutically effective amount of an amphiphilic dendrimer complexed with a Bcl3 siRNA having the sequence of SEQ ID NO: 1.

5. The method of claim 4, wherein the cancer is nasopharyngeal carcinoma (NPC).

6. The method of claim 4, wherein the siRNA and the amphiphilic dendrimer have an N/P ratio of 2.5 to 15, 5 to 15, or 5 to 10.

7. The method of claim 6, wherein the siRNA and the amphiphilic dendrimer have the N/P ratio of about 5.

8. The method of claim 4, wherein the pharmaceutically effective amount of the amphiphilic dendrimer complexed with a Bcl3 siRNA produces Bcl3 siRNA concentration in the subject's body of 2.5 nM to 50 nM, 10 nM to 50 nM, or 20 nM to 50 nM.

9. The method of claim 8, wherein the pharmaceutically effective amount of the amphiphilic dendrimer complexed with a Bcl3 siRNA produces Bcl3 siRNA concentration in the subject's body of about 10 nM or 20 nM.

* * * * *